United States Patent
Leschinsky et al.

(12)

(10) Patent No.: US 11,123,256 B1
(45) Date of Patent: Sep. 21, 2021

(54) SYSTEMS AND METHODS FOR DELIVERY OF REPEATED REMOTE ISCHEMIC CONDITIONING AND MONITORING COMPLIANCE

(71) Applicant: LifeCuff Technologies Inc., Waldwick, NJ (US)

(72) Inventors: Boris Leschinsky, Mahwah, NJ (US); Thomas A Moore, Philadelphia, PA (US); Abe Abramovich, Lawrenceville, NJ (US)

(73) Assignee: LifeCuff Technologies Inc., Waldwick, NJ (US)

( * ) Notice: Subject to any disclaimer, the term of this patent is extended or adjusted under 35 U.S.C. 154(b) by 0 days.

(21) Appl. No.: 17/239,627

(22) Filed: Apr. 25, 2021

(51) Int. Cl.
  *A61H 9/00* (2006.01)
  *A61B 5/00* (2006.01)
  *G16H 20/40* (2018.01)

(52) U.S. Cl.
  CPC ......... *A61H 9/0092* (2013.01); *A61B 5/4833* (2013.01); *G16H 20/40* (2018.01); *A61H 2201/501* (2013.01); *A61H 2209/00* (2013.01); *A61H 2230/04* (2013.01); *A61H 2230/202* (2013.01); *A61H 2230/207* (2013.01); *A61H 2230/42* (2013.01); *A61H 2230/50* (2013.01)

(58) Field of Classification Search
  CPC ........ A61B 5/4833; A61H 9/00; A61H 9/005; A61H 9/0092; A61H 2230/202; A61H 2230/207; A61H 2230/04; A61H 2230/42; A61H 2230/50; A61H 2201/50; A61H 2201/501; A61H 2201/5012; A61H 2201/5007; A61J 7/0445
  See application file for complete search history.

(56) References Cited

U.S. PATENT DOCUMENTS

| 7,717,855 | B2 | 5/2010 | Caldarone |
| 8,114,026 | B2 | 2/2012 | Leschinsky |
| 8,246,548 | B2 | 8/2012 | Naghavi |
| 8,753,283 | B2 | 6/2014 | Leschinsky |
| 8,764,789 | B2 | 7/2014 | Ganske |
| 8,790,266 | B2 | 7/2014 | Caldarone |
| 8,795,323 | B2 | 8/2014 | Leschinsky |
| 8,911,469 | B2 | 12/2014 | Raheman |
| 8,974,491 | B2 | 3/2015 | Leschinsky |
| 8,986,342 | B2 | 3/2015 | Naghavi |
| 2002/0013516 | A1* | 1/2002 | Freyre .................... G16H 20/30 600/300 |

(Continued)

OTHER PUBLICATIONS

Grieveson, S. 2003, "Intermittent pneumatic compression pump settings for the optimum reduction of oedema", Journal of Tissue Viability, vol. 13, No. 3, pp. 98-110. (Year: 2003).*

(Continued)

*Primary Examiner* — Colin W Stuart
*Assistant Examiner* — Douglas Y Sul
(74) *Attorney, Agent, or Firm* — Boris Leschinsky

(57) ABSTRACT

A system for automated delivery and monitoring compliance for repeated remote ischemic conditioning treatments incudes at least one device for automated delivery of the therapy and at least one communications module to collect and record usage data. Reports of subject compliance with a predetermined schedule of therapy delivery is transmitted to the central database and a prescribing physician.

19 Claims, 1 Drawing Sheet

(56) References Cited

U.S. PATENT DOCUMENTS

| | | | |
|---|---|---|---|
| 2007/0100667 A1* | 5/2007 | Bardy | G16H 10/60 |
| | | | 705/3 |
| 2007/0160645 A1 | 7/2007 | Vinten-Johansen | |
| 2008/0139949 A1 | 6/2008 | Caldarone | |
| 2009/0137884 A1 | 5/2009 | Naghavi | |
| 2009/0287069 A1 | 11/2009 | Naghavi | |
| 2010/0105993 A1 | 4/2010 | Naghavi | |
| 2010/0160799 A1 | 6/2010 | Caldarone | |
| 2010/0185220 A1 | 7/2010 | Naghavi | |
| 2010/0305607 A1 | 12/2010 | Caldarone | |
| 2010/0324429 A1 | 12/2010 | Leschinsky | |
| 2011/0190807 A1 | 8/2011 | Redington | |
| 2011/0208099 A1 | 8/2011 | Naghavi | |
| 2011/0240043 A1 | 10/2011 | Redington | |
| 2011/0251635 A1 | 10/2011 | Caldarone | |
| 2011/0319732 A1 | 12/2011 | Naghavi | |
| 2012/0130419 A1 | 5/2012 | Leschinsky | |
| 2012/0157889 A1* | 6/2012 | Tanis | A61B 5/4833 |
| | | | 601/2 |
| 2012/0265240 A1 | 10/2012 | Ganske | |
| 2012/0277789 A1 | 11/2012 | Caldarone | |
| 2013/0184745 A1 | 7/2013 | Leschinsky | |
| 2013/0204106 A1* | 8/2013 | Bennett | A61B 5/486 |
| | | | 600/324 |
| 2014/0200464 A1 | 7/2014 | Webster | |
| 2014/0296756 A1 | 10/2014 | Ganske | |
| 2014/0296757 A1 | 10/2014 | Leschinsky | |
| 2015/0265286 A1 | 9/2015 | Raheman | |
| 2015/0272825 A1* | 10/2015 | Lim | G07C 9/38 |
| | | | 340/5.2 |
| 2016/0166464 A1* | 6/2016 | Douglas | A61H 9/0078 |
| | | | 601/148 |
| 2018/0200140 A1* | 7/2018 | Ganske | B32B 5/26 |
| 2018/0272147 A1 | 9/2018 | Freeman | |
| 2020/0241683 A1* | 7/2020 | Le | A61H 7/007 |
| 2021/0015698 A1* | 1/2021 | Spyropoulos | A61H 9/0092 |

OTHER PUBLICATIONS

Berry B.E., Pinard A. E. Assessing Tissue Oxygenation. Critical Care Nurse vol. 22, No. 3, Jun. 2002, pp. 22-40.

Walsh SR, Tang T, Sadat U, Dutka DP, Gaunt ME. Cardioprotection by remote ischaemic preconditioning. Br J Anaesthesia 99;5:611-616, 2007.

Hausenloy DJ, Yellon DM. Remote ischaemic preconditioning: underlying mechanisms and clinical application. Cardiovasc Res 79:377-386, 2008.

Tapuria N, Kumar Y, Habib MM, Amara MA, Seifalian AM, Davidson BR. Remote ischemic preconditioning: a novel protective method from ischemia reperfusion injury—a review. J Surg Res 150;2:304-330, 2008.

Birnbaum Y, Hale SL, Kloner RA. Ischemic preconditioning at a distance. Circulation, 96:1641-1646, 1997.

Kharbanda RK, Nielsen TT, Redington AN. Translation of remote ischaemic preconditioning into clinical practice. Lancet 374:1557-1565, 2009.

Xiong J, Liao X, Xue FS, Yuan YJ, Wang Q, Liu JH. Remote ischemia conditioning—an endogenous cardioprotective strategy from outside the heart. Chin Med J 124(14):2209-2215, 2011.

Szijártó A, Czigány Z, Turóczi Z, Harsányi L. Remote ischemic preconditioning—a simple, low-risk method to decrease ischemic reperfusion injury: models, protocols and mechanistic background. A review. J Surg Res. 178, 797-806, 2012.

Lim SY, Hausenloy DJ. Remote ischemic conditioning: from bench to bedside. Front Physio 3:27, 2012.

Heusch G, Bøtker HE, Przyklenk K, Redington A, Yellon D. Remote ischemic conditioning. J Am Coll Cardiol 65 (2):177-195, 2015.

Sivaraman V, Pickard JMJ, Hausenloy DJ. Remote ischaemic conditioning: cardiac protection from afar. Anaesthesia 2015. First published online Feb. 26, 2015.

Grieveson S. Intermittent pneumatic compression pump settings for the optimum reduction of oedema. Journal of Tissue Viability vol. 13, No. 3, Jul. 2003, pp. 98-110.

* cited by examiner

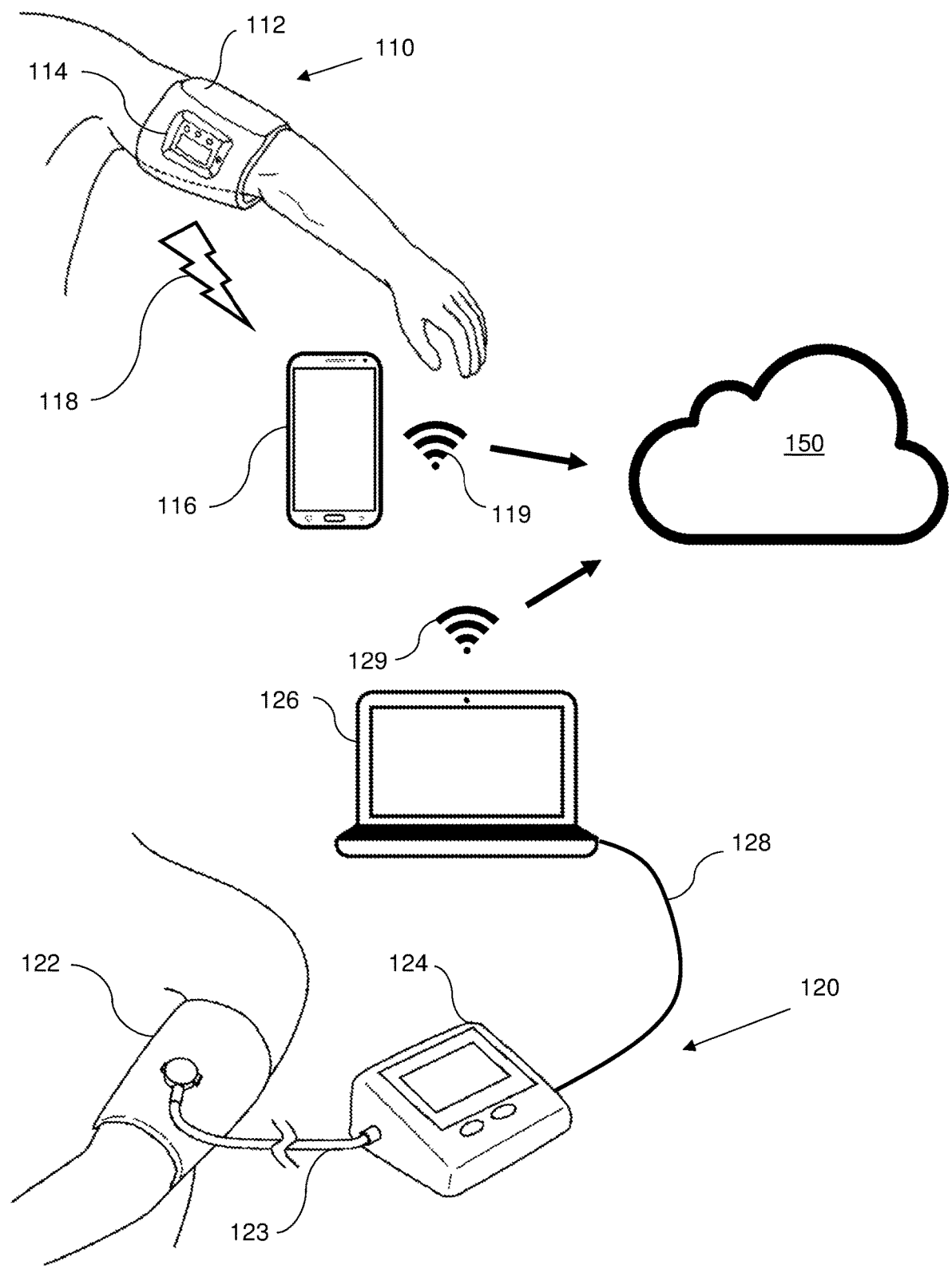

SYSTEMS AND METHODS FOR DELIVERY OF REPEATED REMOTE ISCHEMIC CONDITIONING AND MONITORING COMPLIANCE

BACKGROUND

Without limiting the scope of the invention, its background is described in connection with systems and methods for automated delivery of a therapy called Repeated Remote Ischemic Conditioning (rRIC). More particularly, the invention describes automated devices equipped with communications modules connecting to a central database configuring for monitoring compliance of subjects with receiving rRIC treatments as prescribed.

A general concept of ischemic conditioning was first discovered by Murray in 1980's and involves applying a series of non-lethal ischemic episodes to a target tissue making it resistant for a certain period afterwards to a more serious ischemic stress. Initially applied to the heart, ischemic conditioning benefits were later confirmed for other organs and tissues, including brain, kidneys, stomach, skin, etc.

Remote ischemic conditioning (RIC) is a variation of the ischemic conditioning therapy where a series of sub-lethal ischemic stress periods is applied to a tissue other than a target tissue marked for subsequent protection, namely to an extremity such as an upper arm. This variation was a welcomed development in that it allowed applying RIC non-invasively. It was also discovered that RIC benefits may be elicited even when the therapy is applied after the index ischemic event, which may occur unpredictably, such as a myocardial infarction or a stroke. This discovery made RIC even more practical for use and led to a broad range of clinical investigations into a variety of ischemic conditions affecting many different organs and tissues.

Most recently, a further discovery was made that multiple applications of RIC distributed over time, rather than a single administration after an index ischemic event, may convey additional benefits for a variety of chronic ailments as compared with a single RIC therapy. This version of the therapy is called Repeated Remote Ischemic Conditioning (rRIC) or Chronic Remote Ischemic Conditioning, which for the purposes of this invention is used interchangeably. Other terminology was also used in recent literature to describe a series of RIC applications over time, which are also included under a general term "rRIC" for the purposes of this application.

Conventional RIC therapy may be applied using an inflatable cuff, tightly wrapped around at least one extremity of a subject, such as an upper arm or a thigh. Some investigators investigated using two or more extremities (such as both upper arms) at the same time. Regardless of how many extremities are used for RIC delivery, manually inflating and deflating one or more cuffs multiple times over a prescribed period of time is a tedious and time-consuming process. A number of automated devices were developed to apply RIC to a subject. Using automated devices allows a more convenient and repeatable delivery of RIC, as opposed to early applications using a manually inflatable cuff. These devices are generally configured to automatically apply appropriately high cuff pressure to sufficiently reduce or completely arrest blood flow in an extremity of the subject for prescribed periods of time. Examples of such devices may be found in several US patents by one of the inventors of this patent application, for example U.S. Pat. Nos. 10,624,649, 9,950,009, 9,801,780, 9,611,476, 9,610,213, 8,974,491, and 8,795,323, incorporated herein in their respective entireties by reference.

For subjects in need of multiple applications of RIC over time, services of a visiting nurse may be utilized to deliver RIC at the homes of these subjects, as many of them may have difficulty visiting a healthcare facility on their own. Recently, as at least some of these devices are improved further to deliver the therapy of remote ischemic conditioning in a very safe and non-invasive manner, it become more advantageous to instruct each subject to self-administer the RIC therapy at home. This is based on the notion that using these automated RIC machines, especially those described in the cited above patents, may not be much more complicated than using a variety of commonly available home blood pressure monitors. In these cases, the subject is instructed to apply a cuff to an upper arm and simply press a START button. The rest of the process may proceed automatically and controlled by an internal device controller, which may be configured to apply sufficient pressure to the cuff which is effective for RIC purposes.

Repeated RIC therapies are most effective when applied at intervals as prescribed by a physician. Applying too many RIC therapies close together or spaced apart too far or, in other cases, skipping prescribed RIC sessions from time to time may diminish the overall efficacy of the treatment. When a subject is attended by a healthcare provider such as a nurse or a physician, monitoring compliance is reasonably straight forward. However, when the subject is asked to self-administer the therapy at home or elsewhere outside the doctor's office, accurate reporting of therapy delivery is more challenging.

The need exists therefore for a new system and a new method for applying repeated RIC therapies and providing more objective monitoring of the subject properly following a prescribed regiment of RIC therapies.

The need also exists for a new system and a new method of collecting usage information including vital sign monitoring, which may provide additional benefit for the well-being of the subject on top of the direct benefit of rRIC.

SUMMARY

Accordingly, it is an object of the present invention to overcome these and other drawbacks of the prior art by providing a novel system and a novel method of applying a series of repeated remote ischemic conditioning treatments to a subject by using an automated device and collecting usage data therefrom.

It is another object of the present invention to provide a novel system and a novel method for applying repeated remote ischemic conditioning treatments to a subject and collecting vital signs such as heart rate or blood pressure, followed by reporting the usage data and vital signs to a central database, configured for storing the data and optionally reporting it further to a care provider.

It is a further object of the present invention to provide novel systems and novel methods of applying rRIC to a subject including monitoring compliance with the prescribed schedule of rRIC applications, wherein an alert message may be automatically generated upon detection of a deviation of RIC therapy sessions from a predetermined schedule.

It is yet a further object of the present invention to provide a central database configured to receive and report usage data and compliance with prescribed schedules of RIC applications for a multitude of subjects in need of rRIC.

The novel system of automated application of rRIC and monitoring compliance may comprise an automated remote ischemic conditioning device configured for delivery of remote ischemic conditioning therapy by periodically inflating and deflating an inflatable cuff according to a predetermined schedule of inflations and deflations. The system may further comprise a communications module operably associated with the remote ischemic conditioning device and configured to collect and report usage data therefrom including time and date of use. The communications module may be further configured to compare the usage data against the predetermined schedule of delivery of remote ischemic conditioning treatments and, upon detection of a deviation therefrom, generate an alert message, whereby facilitating compliance monitoring of delivery of the repeated remote ischemic conditioning treatments.

A central database for collecting reports from one or more automated devices for rRIC delivery may also be provided and configured to generate reports that may be sent to respective prescribing physicians with usage data information and vital sign information for the rRIC subject. Deviations from prescribed schedule of rRIC may also be sent to subjects themselves with a copy to designated family members or other caregivers prompting them to interfere and correct the situation.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 1 is a schematic view of the main components of the present invention.

DETAILED DESCRIPTION OF PREFERRED EMBODIMENTS OF THE INVENTION

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

FIG. 1 shows a general view of the main components of the system of the present invention. A system for automated delivery of remote ischemic conditioning may include a first automated device 110, which in turn may include a first inflatable cuff 112 configured to be positioned tightly around an upper arm of a first subject. A first controller 114 may be built onto or otherwise operably attached to the inflatable cuff 112 and configured to inflate and deflate the inflatable cuff according to a first predetermined schedule of inflations and deflations of the cuff to deliver remote ischemic conditioning therapy.

The design details of the automated device 110 may be found in our previously filed patent applications and issued patents as described above. Briefly, the first controller 114 may include an air pump operated, for example, using a rechargeable battery or connected to a wall electrical outlet. The air pump may be configured to inflate the inflatable cuff via a pneumatic line, which in turn may feature at least one valve configured upon activation to dump air pressure from the cuff to atmosphere. The same valve may be operated to bleed down the air pressure more slowly in order to enable detection of blood pressure, for example by using oscillometric blood pressure determination techniques. The first controller 114 may be further equipped with a display for user interface purposes as well as a START button configured to initiate the delivery of the remote ischemic conditioning therapy. In other embodiments, the entire user interface as well as operation of the device may be controlled using the first communication module 116 such as a smartphone or alike as the invention is not limited in this regard.

A first communications module 116, such as a smartphone may be operatively associated with the first controller 114, for example by a Bluetooth link 118 and configured to collect and optionally, report the first usage data via a wireless Internet connection 119 to a central database server 150. The first usage data may include date and time of therapy delivery as well as at least one hemodynamic or another physiologic parameter, such as a blood pressure or a heart rate of the subject.

A suitable user interface may be provided with the automated remote ischemic conditioning device and/or the first communications module. The user interface may include in some examples a touchscreen or another display showing a calendar of scheduled sessions of RIC delivery. In other examples, a history of scheduled, delivered, and missed RIC sessions may also be displayed, along with the indicator of compliance of RIC delivery with a predetermined schedule of RIC sessions. The RIC therapy may be initiated, paused, stopped or aborted by operating an appropriate control on user interface located on the automatic device or the first communications module. Redundant controls on both the automatic device and the first communications module are also envisioned.

An alternative arrangement of components of the system for delivering a series of remote ischemic conditioning treatments and monitor compliance is also seen in FIG. 1. It includes a second automated remote ischemic conditioning device 120, which in turn includes a second inflatable cuff 122 operatively attached to a second controller 124, for example via a pneumatic tube 123. A stand-alone controller 124, as illustrated in this case, may include similar functional components as the first controller 114, but in this case may be optionally configured to be powered from a wall outlet and may include additional features, for example a dedicated mode for measuring blood pressure of the subject. FIG. 1 further shows the second controller 124 connected to a second communications module 126, in this case via a cable 128. The second communication module 126, for example a personal computer or a laptop, may be further configured to communicate the second usage data collected from the second controller 124 via a wireless or wired connection 129 such as a connection via the Internet, to the central database 150.

Other arrangements are also conceived of for the purposes of the present invention. In embodiments, the first communications module may be designed as a first electronic device running a dedicated software program, that may be suitable for such operation. In embodiments, the first electronic device may be a cellular phone, a smartphone, a personal computer, a tablet, a smartwatch, a home wireless network component such as Alexa or Google assistant speaker or alike, or a dedicated electronic module built into or operatively connected to the first remote ischemic conditioning device. In addition, the first electronic device may be configured to communicate with the first controller via a wired connection or a variety of wireless communication protocols including WiFi, Bluetooth, ZigBee, Z-Wave, 6LoWPAN, Thread, cellular, 2G, 3G, 4G, 5G, LTE, NFC, etc. as the invention is not limited in this regard. The first communications module may also be configured to collect and, at least in some examples, report the first usage data to the central database. Reporting of usage data can be accomplished by a variety of wired and wireless data transmission protocols, for example those mentioned above, as the invention is not limited in this regard.

In further embodiments, the system of the invention may include additional automated devices and corresponding communication modules, all configured to deliver rRIC to additional subjects.

The therapy of remote ischemic conditioning may be characterized, at least in part, by a number of alternating periods of cuff inflation and deflation. Some or all periods of cuff inflation and/or cuff deflation may last anywhere between about 2 min and about 15 min, for example 2, 3, 4, 5, 6, 7, 8, 9, 10, 11, 12, 13, 14, 15 min or any duration inbetween. There may be as little as 3 periods of cuff inflation alternating with cuff deflation, or a many as 10 cuff inflation periods, such as 3, 4, 5, 6, 7, 8, 9, or 10 such periods as the invention is not limited in this regard. In a most typical case, there may be 3 or 4 periods of cuff inflation alternating with cuff deflation, each lasting about 4-5 minutes, so that the entire therapy of remote ischemic conditioning may take approximately 30-45 minutes from start to finish.

The pressure of cuff inflation during the periods of cuff occlusion may be selected to be sufficient to at least partially or completely occlude blood flow in an extremity equipped with the inflatable cuff so as to invoke a temporary limb ischemia, which is sufficiently strong to elicit the benefits of remote ischemic conditioning. Various methods and devices to apply such cuff inflation pressure for the purposes of remote ischemic conditioning are described in our previously cited patents. The controller of the automated remote ischemic conditioning device may be equipped with one or more redundant safety features (both in hardware and software) to assure safe delivery of the therapy to the subject, such as in some examples, features designed to not exceed a predetermined maximum inflation pressure or a predetermined maximum duration of limb ischemia interval.

Repeated remote ischemic conditioning is a more recently discovered therapy in which individual sessions of remote ischemic conditioning treatment as described above are repeated from time to time. Such repetition may happen on a periodic basis such as 2, 3, 4, or 5 times a day, or once a day, once every two days, once every three days, once every four days, once every five days, once every six days, once every seven days, once every eight days, once every nine days, once every ten days, once every eleven days, once every twelve days, once every thirteen days, once every fourteen days, once every fifteen days, or even less frequently as the invention is not limited in this regard.

Similarly, a total number of repeated applications of remote ischemic conditioning therapies constituting an entire rRIC series may vary from 2 to 100 or more, such as 2, 4, 6, 10, 15, 20, 25, 30, 35, 40, 45, 50, 60, 70, 80, 90, 100 of any number in between as the invention is not limited in this regard.

Both the frequency and the total number of RIC therapies as well as an individual schedule of each RIC therapy may be determined by a prescribing physician. A user interface of the automated remote ischemic conditioning device or, in the alternative, a user interface of the communications module may be configured to automatically transform the input received from a physician or an authorized caregiver (which may contain the details of the predetermined RIC therapy as well as the prescribed number and frequency of RIC therapies constituting an overall rRIC series of therapies) into a predetermined first schedule of RIC therapies as described now in greater detail below.

Once the schedule of cuff inflations and deflation for each RIC therapy has been established based on a prescription from a physician or using a default most commonly used schedule of 4 cycles of 5 min inflation and 5 min deflation, the user interface may be operated to input a desired frequency and total number of RIC treatments in the rRIC series.

It may be more convenient for the subject to schedule RIC therapy delivery during waking hours. To achieve that, the user interface and the rRIC software may be configured to use default waking hours, such as for example from 8 am to 10 pm, or in the alternative, to allow the user to enter or adjust the waking hours for the subject. In further embodiments, certain waking hours of the day may be further blocked off so that no RIC therapy is scheduled during these blocked off hours.

Following the determination of the first day of rRIC delivery, the system may be configured to determine a preferred schedule of RIC therapy deliveries. As an example, if the subject requires 3 RIC therapies a week for a total of 12 weeks, that is a total of 36 therapies lasting at most an hour each and spread over 84 days. Simple division of 84 days by 36 therapies would indicate a new RIC therapy is required every 2⅓ day, or once every 56 hours. Inevitably, strict adherence to this simple schedule will interfere with night sleep hours of other blocked off hours making it undesirable. The system of the present invention may be configured to adjust the schedule appropriately and without compromising too much the extent of periodicity of the therapy deliveries. One exemplary approach for such adjustment may be to schedule a RIC delivery in any available hours during the target delivery day.

Using the example above, the system of the invention may be configured to provide windows of allowed time intervals for initiating RIC therapies. Starting on day 1, for example, the first allowed time interval may be between 8 am and 12 pm to give the subject at least some flexibility within this time interval to initiate the therapy of remote ischemic conditioning. The second scheduled therapy would be slated ideally 56 hours after the middle of the first allowed time interval, 10 am in this example. That would put the start of the second therapy at 6 pm on the third day after the start of the first rRIC procedure. In this case, the system may be configured to define the second allowed time interval as 4 pm to 8 pm—again to allow the subject some scheduling flexibility.

The third scheduled RIC therapy would fall to 2 am of the respective third day after the previous therapy, which would interfere with the sleeping hours of the subject. An adjustment to the next available waking hours period of 8 am and 12 pm would put the schedule back on track. The cycle will be then repeated until all 36 therapies are delivered during morning and afternoon hours.

In further embodiments, the system of the invention may be configured to adjust the schedule if one or more scheduled RIC therapies are missed by the subject. In one example, upon detection of a missing instance of the RIC therapy, the system may record a deviation from the predetermined first schedule and shift the remaining scheduled therapies by the necessary number of days to account for the missing time. Such adjustment may be done using the same RIC frequency for the remaining period if time as was used at the beginning of rRIC therapy. The number of such missed days allowed to be used for lengthening the overall rRIC time interval may be between 1 and 15 days, for example 1, 2, 3, 4, 5, 6, 7, 8, 9, 10, 11, 12, 13, 14, or 15 days. If more than a certain predetermined number of days has passed in the middle of the rRIC schedule without a scheduled RIC delivery, the entire therapy delivery schedule may be restarted as the long break in the therapies may compromise the ability of the therapy to provide the subject with the benefits of rRIC. In some examples, this maximum predetermined number of days missed between successive RIC therapies may be anywhere from 5 to 20, or more if that is specified by the prescribing physician, as the invention is not limited in this regard. The system of the invention may feature a default maximum number of missed days, for example 10 days, but may also allow the user to provide a desired adjustment.

Once the predetermined schedule of rRIC therapy deliveries is established, the system of the invention may be configured to monitor compliance of the subject with such scheduled RIC therapy deliveries. In one example, the system of the invention may be configured to produce a reminder message for some or all upcoming RIC therapies, such as 1 hour before the allowed window of time for each therapy. In other examples, a reminder message may be generated 1 hour before the end of the allowed time to still provide an opportunity to start and finish the therapy and adhere to the schedule. Such reminders may be done in a number of ways, including a visual message on a display of the first electronic device, an audio chime, a text message or another electronic communication to the subject and/or a designated caregiver, as the system may be adjusted to suit individual subject preferences.

Compliance monitoring may be done by comparing each verified completed RIC therapy to the predetermined schedule of such therapies. Deviation of the RIC therapy deliveries from the predetermined schedule may also be reported to the subject, a caregiver, and/or a prescribing physician using any of the communication modes described above.

The system may be further configured to automatically detect the date and time of a full delivery of the RIC therapy and distinguish that event from incomplete RIC therapies. In some examples of the system, verification of completion may be done by verifying the total duration of each of the cuff inflation and deflation cycles as corresponding to the scheduled durations and/or by confirming that each time the cuff is inflated, the cuff pressure is maintained within reasonable physiologically acceptable values, for example above 50 mmHg and below 250 mmHg.

Usage data generated during each RIC therapy delivery may include at least the date and time of RIC delivery along with a positive confirmation that the entire RIC procedure is successfully completed. In other examples, a more complete record of RIC parameters and hemodynamic values measured during RIC cycles may also be included in the usage data report. Such additional hemodynamic parameters may include systolic blood pressure, diastolic blood pressure, mean arterial pressure, heart rate, etc—as measured at least once or a number of times before, during, or after the RIC procedure.

In further embodiments, the first electronic device or the RIC controller may be further equipped to collect additional physiological data, such as ECG, temperature, respiration rate, pulse oximetry or $SpO_2$, blood glucose, etc and include this data together with the RIC report and with other physiologic and hemodynamic parameters. In some embodiments, suitable sensors for collecting this physiologic surveillance data may be built into the first automated device or the first electronic device. In other embodiments, one or more suitable sensors may be operably connected to the first RIC controller or the first electronic device via a wired or a wireless communication. The software of the first communications module may be configured to collect and integrate this additional physiologic data into a combined RIC usage data report.

In one example, blood glucose may be measured at the same time as RIC and reported as a single report to the prescribing physician, which may be advantageous for patients suffering from chronic diabetic foot ulcers and treated with rRIC therapies.

Usage data may be reported by the first communication module to the central database, which may be configured to accept and collect usage data for one or more subjects. In some embodiments, usage data may be transmitted after RIC therapy is complete. In other embodiments, usage data may be transmitted live and streamed by the first communication device to the central database as the RIC therapy is progressing. One advantage of a live stream of usage data is the ability for a human monitoring agent, such as a nurse, to verify correctness of the entire process remotely—by securely logging into the live data stream for a subject. Live monitoring of RIC by a remotely located agent may be helpful for training purposes to make sure the subject or a caregiver applies the device and the therapy correctly. Secure remote monitoring in this case avoids the need for the monitoring personnel to be physically present in each home of the subject for each scheduled RIC delivery.

Once the delivery of the scheduled RIC therapy is complete, repeating such therapy shortly thereafter is not necessary. To avoid excessive use of the device and prevent the subject from activating the system too frequently, the first controller or the first electronic device may be configured to temporarily disable activation of the next RIC delivery, for example until the next scheduled allowable time interval.

In additional embodiments, the automated devices for remote ischemic conditioning may be configured to be activated independently of whether it is operatively communicating with the communications module or not. In case of a lack of such communication, the automated device may still be activated for delivery of a full RIC therapy procedure. This event may be recorded in the internal memory of the automated device and later on transmitted to the communications module when the connection between the two is restored. Alternatively, the communications module may be configured to allow a manual entry of the performed but not instantly recorded RIC procedure at a later time. Such manual entry will avoid automatic schedule adjustment, which otherwise may occur once a scheduled RIC procedure is identified as missed by the subject.

In further embodiments, the RIC controller of the communications module associated therewith may comprise a subject selection module. Ability to select the subject may be useful when one controller and one communications module are used to deliver rRIC to more than one subject. This may be the case when rRIC is delivered in a clinic or a doctor's office. Alternatively, this may occur when a visiting nurse attends to more than one subject in need of rRIC.

To facilitate proper separation of rRIC schedules and recorded usage data, a subject selection module may be provided. It can be designed to be a part of the initial setup of the device or can be activated at a later point when more than one subject is in need of RIC. Each subject may be associated with a separate virtual folder, containing the details of the prescribed rRIC protocol and the individual details of RIC therapy deliveries.

A cumulative schedule of all RIC procedures may be displayed for the user so as to understand the timing of all upcoming RIC procedures and subjects associated with each one of these procedures. Once the time for the next procedure comes, the user may have an option to select the proper subject and associate the RIC procedure with that subject. The system of the invention may be further configured to generate individual alert messages when a deviation from a prescribed RIC schedule is detected for a particular subject.

In other yet embodiments, the central database may be configured to transmit some or all of the subject's health data to another database, for example that of a hospital system so as to provide a necessary rRIC record and other health related measurements to become a part of the overall digital health record of the subject.

Additional examples of the system may include configuring the central database to accept and synchronize the schedule of rRIC procedures and updates as to delivered procedures for the same subject when using multiple automated devices and communications modules for the same subject. This situation may be encountered, for example, when the subject receives some RIC therapies at home and other RIC therapies at the doctor's office. In this case, each RIC therapy may be recorded at the central database in real time or shortly after its completion and the record of the subject may be synchronized between all automated devices and communication modules used to service the rRIC schedule for the subject.

In further yet embodiments, the system may include a mode selection switch, for example provided with the automated device for remote ischemic conditioning, or in alternatively, provided with the first communications module. At least two modes of operation may be provided to choose from: (i) remote ischemic conditioning mode, and (ii) blood pressure monitoring mode. The user, caregiver, or other authorized personnel may select the first mode of RIC delivery to provide the subject with the health benefits of RIC therapies. Prior to, during, or after the completion of the scheduled series of RIC deliveries in mode (i), mode (ii) may be activated to keep track of the subject' blood pressure, heart rate, or other physiologic parameters as listed above. The record of these measurements may be collected by the first communication module and transmitted to the central database, prescribing physician, or another interested party. One benefit of operating the automated device in one of these two modes is the ability to continue remote physiologic surveillance of the wellbeing of the subject during and after the completion of the rRIC procedures.

Additional sensors and/or health monitoring modules may be provided along with the system of the invention to facilitate monitoring such other hemodynamic and physiologic parameters. These sensors may be configured for plug-in, wired or wireless communication with either the automated device for RIC delivery or the communication module operatively associated therewith. The system of the invention may also be configured to operate with independent third-party sensors and health monitoring modules so as to collect all health-related information about the subject, transmit it to the subject's record at the central database, and present it to the prescribing physician or another authorized interested party. All internal communications between system components as well as with the central database server may be conducted using suitable encryption or other means to protect subject' privacy and avoid unauthorized data access.

In further alternative embodiments, both the rRIC mode and health monitor mode may be operated at the same time, for example with different start buttons for (i) initiating a RIC procedure and (ii) initiating a blood pressure measurement. A cumulative record of RIC procedures, blood pressure measurements as well as other health parameter measurements may be accumulated by the automated device and/or the communications module and transmitted to the central database.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. Incorporation by reference is limited such that no subject matter is incorporated that is contrary to the explicit disclosure herein, no claims included in the documents are incorporated by reference herein, and any definitions provided in the documents are not incorporated by reference herein unless expressly included herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, Aft AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, Aft BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A system for delivering a series of repeated remote ischemic conditioning treatments and monitor compliance, the system comprising:

i. a first automated remote ischemic conditioning device configured for delivery of remote ischemic conditioning therapy to a first subject by periodically inflating and deflating an inflatable cuff according to a first predetermined schedule of repeated delivery of remote ischemic conditioning treatments, and ii. a first communications module operably associated with the first remote ischemic conditioning device and configured to non-invasively collect a first usage data therefrom including time and date of use, wherein the first communications module is configured to compare the first usage data against the first predetermined schedule of repeated delivery of remote ischemic conditioning treatments and, upon detection of a deviation therefrom, generate an alert message, thereby facilitating compliance monitoring of delivery of repeated remote ischemic conditioning treatments, wherein the first communications module is further configured to generate the first predetermined schedule of repeated delivery of remote ischemic conditioning treatments during default or user-adjusted waking hours prior to initiating thereof using a prescribed number of treatments and a prescribed frequency of treatments, wherein the first predetermined schedule comprises a series of allowed time intervals, each allowed time interval is allocated for each respective remote ischemic conditioning treatment, at least one of said allowed time intervals is longer in duration than a respective remote ischemic conditioning treatment to provide scheduling flexibility.

2. The system as in claim 1, wherein following a verified completion of each remote ischemic conditioning treatment within a corresponding allowed time interval, the first remote ischemic conditioning device or the first communications module is further configured to disable activation of the first remote ischemic conditioning device until the beginning of a next allowed time interval, whereby avoiding untimely application of remote ischemic conditioning treatment outside the first predetermined schedule of repeated delivery of remote ischemic conditioning treatments.

3. The system as in claim 1, wherein upon resumption of usage of the first remote ischemic conditioning device after detecting an instance when a scheduled remote ischemic conditioning treatment is not completed, the first communications module is further configured to lengthen a remaining portion of the first predetermined schedule of repeated delivery of remote ischemic conditioning treatments by 1 to 15 days using the same intervals between treatments as prior to a missed or incomplete scheduled treatment.

4. The system as in claim 1, wherein the first communications module is further configured to generate reminder messages prior to a beginning or prior to an end of a next allowed time interval to prompt performing a scheduled remote ischemic conditioning treatment without deviating from the first predetermined schedule.

5. The system as in claim 1, wherein the first communications module is a first electronic device operatively communicating with the first remote ischemic conditioning device, the first electronic device operated by a software program to perform all required functions of the first communications module.

6. The system as in claim 5, wherein the first electronic device is a home wireless network component operatively associated with the first remote ischemic conditioning device.

7. The system as in claim 1, wherein the first remote ischemic conditioning device is further configured to non-invasively detect and record at least one hemodynamic parameter of the first subject when delivering each remote ischemic conditioning treatment.

8. The system as in claim 7, wherein the at least one hemodynamic parameter detected during cuff inflation of each remote conditioning treatment is a heart rate of the first subject or an arterial blood pressure of the first subject.

9. The system as in claim 1 further comprising at least one physiologic sensor configured to non-invasively detect at least one physiologic parameter of the first subject.

10. The system as in claim 9, wherein the physiologic parameter is selected from a group consisting of ECG, body temperature, respiration rate, and blood glucose level.

11. The system as in claim 1, wherein the first communications module is configured to report the first usage data, the system further comprising a central database configured to receive and record the first usage data reported by the first communications module.

12. The system as in claim 11 further comprising additional remote ischemic conditioning devices configured for delivery of remote ischemic conditioning therapy to additional subjects, the system further comprising additional communications modules operably associated with corresponding remote ischemic conditioning devices and configured to collect corresponding additional usage data for the additional subjects therefrom.

13. The system as in claim 12 further configured for reporting of usage data, at least one non-invasive hemodynamic parameter, and at least one physiologic parameter for at least one, some, or all of the first subject and the additional subjects to the central database.

14. The system as in claim 1, wherein the first remote ischemic conditioning device or the first communications module comprises a subject selection module, whereby the system is further configured, upon operating the subject selection module, to deliver repeated remote ischemic conditioning treatments to a selected first, second or more subjects by following a respective first, second or more predetermined schedules of delivery of remote ischemic conditioning treatments as well as non-invasively collect and report a first, second or more usage data therefrom, thereby facilitating easy transport of the first remote ischemic conditioning device and the first communications module between selected first, second, and more subjects.

15. The system as in claim 1, wherein the first communications module is configured to verify completion of each scheduled remote ischemic conditioning treatment by:
  i. verifying duration of inflatable cuff inflation and deflation cycles in each remote ischemic conditioning treatment as corresponding to scheduled durations of inflatable cuff inflation and deflation cycles according to the first predetermined schedule, and
  ii. verifying that cuff inflation pressure during each cuff inflation cycle is above 50 mmHg and below 250 mmHg.

16. A system for delivering a series of repeated remote ischemic conditioning treatments and monitor compliance, the system comprising:
  i. a first automated remote ischemic conditioning device configured for delivery of remote ischemic conditioning therapy to a first subject by periodically inflating and deflating an inflatable cuff according to a first predetermined schedule of repeated delivery of remote ischemic conditioning treatments,
  ii. a first communications module operably associated with the first remote ischemic conditioning device and configured to non-invasively collect and report a first usage data therefrom including time and date of use, and
  iii. a central database configured to receive the first usage data from the first communications module,
    wherein the first communications module or the central database is configured to compare the first usage data against the first predetermined schedule of repeated delivery of remote ischemic conditioning treatments and, upon detection of a deviation therefrom, generate an alert message, thereby facilitating compliance monitoring of delivery of repeated remote ischemic conditioning treatments,
    wherein the first predetermined schedule comprises a series of allowed time intervals, each allowed time interval is allocated for each respective remote ischemic conditioning treatment, at least one of said allowed time intervals is longer in duration than a respective remote ischemic conditioning treatment to provide scheduling flexibility.

17. A method for delivering a series of repeated remote ischemic conditioning treatments and monitor compliance of such delivery to a first subject, the method comprising the following steps:
  i. providing the first subject with a first automated remote ischemic conditioning device configured upon each activation to automatically deliver one remote ischemic conditioning treatment,
  ii. providing the first subject with a first communications module operably associated with the first remote ischemic conditioning device and configured to collect usage data therefrom,
  iii. operating the first remote ischemic conditioning device to deliver remote ischemic conditioning treatment to the first subject according to a first predetermined schedule of repeated delivery of remote ischemic conditioning treatments,
    wherein the first predetermined schedule comprises a series of allowed time intervals, each allowed time interval is allocated for each respective remote ischemic conditioning treatment, at least one of said allowed time intervals is longer in duration than a respective remote ischemic conditioning treatment to provide scheduling flexibility,
  iv. operating the first communications module to detect and report first usage data as compared to the first predetermined schedule, and
  v. generating an alert message upon detection of deviation of delivery of remote ischemic conditioning treatment from the first predetermined schedule,
    whereby facilitating compliance of the first subject with scheduled delivery of the series of repeated remote ischemic conditioning treatments.

18. The method as in claim 17 further including a step of providing a central database configured to receive and record non-invasively collected usage data from the first communications module and additional communications modules, each of the additional communications modules operably associated with a respective additional automated remote ischemic conditioning device, whereby the central database is configured to facilitate compliance monitoring of delivery of repeated remote ischemic conditioning treatments to the first and all additional subjects.

19. The method as in claim 18, wherein the first and additional communications modules are further configured to non-invasively collect at least one of an arterial blood pressure, a heart rate, an ECG, a body temperature, a respiration rate, an $SpO_2$ level, and a blood glucose level for the respective first subject associated with the first communications module in step (ii) or additional subjects associated with additional communications modules and report thereof to the central database.

* * * * *